United States Patent
Kakee et al.

(10) Patent No.: US 8,475,381 B2
(45) Date of Patent: Jul. 2, 2013

(54) ULTRASOUND DIAGNOSIS APPARATUS AND METHOD OF SETTING SOUND VELOCITY

(75) Inventors: Akihiro Kakee, Nasushiobara (JP);
Muneki Kataguchi, Nasushiobara (JP);
Kenichi Ichioka, Nasushiobara (JP);
Yasushi Kamewada, Utsunomiya (JP)

(73) Assignees: Kabushiki Kaisha Toshiba, Tokyo (JP);
Toshiba Medical Systems Corporation, Ottawara-shi (JP)

( * ) Notice: Subject to any disclaimer, the term of this patent is extended or adjusted under 35 U.S.C. 154(b) by 358 days.

(21) Appl. No.: 12/824,697

(22) Filed: Jun. 28, 2010

(65) Prior Publication Data

US 2010/0331692 A1 Dec. 30, 2010

(30) Foreign Application Priority Data

Jun. 30, 2009 (JP) ................................. 2009-155477
May 20, 2010 (JP) ................................. 2010-116259

(51) Int. Cl.
*A61B 8/14* (2006.01)

(52) U.S. Cl.
USPC ........... 600/443; 600/449; 600/453; 600/455; 600/459

(58) Field of Classification Search
USPC .................. 600/449, 453, 455, 458, 459, 443
See application file for complete search history.

(56) References Cited

U.S. PATENT DOCUMENTS

| | | | | |
|---|---|---|---|---|
| 5,363,851 A * | 11/1994 | Hall et al. | ...................... | 600/455 |
| 6,245,019 B1 * | 6/2001 | Kamiyama | .................... | 600/458 |
| 2003/0092990 A1 * | 5/2003 | Baba et al. | .................... | 600/443 |
| 2004/0133106 A1 * | 7/2004 | Kakee et al. | ................... | 600/437 |
| 2008/0108901 A1 * | 5/2008 | Baba et al. | ..................... | 600/459 |
| 2008/0242999 A1 | 10/2008 | Kakee | | |
| 2009/0088637 A1 * | 4/2009 | Mikami | ........................ | 600/443 |
| 2009/0163815 A1 * | 6/2009 | Kawagishi et al. | ........... | 600/453 |

FOREIGN PATENT DOCUMENTS

| | | |
|---|---|---|
| CN | 101406401 A | 4/2009 |
| JP | 2008-264531 | 11/2008 |

OTHER PUBLICATIONS

Chinese Office Action issued Mar. 7, 2012 in patent application No. 201010214897.X.

* cited by examiner

*Primary Examiner* — Baisakhi Roy

(74) *Attorney, Agent, or Firm* — Oblon, Spivak, McClelland, Maier & Neustadt, L.L.P.

(57) ABSTRACT

In one embodiment, an ultrasonic diagnostic apparatus includes an image creating unit, an image-creation control unit and a display control unit. The image creating unit creates an ultrasound image from data created by adding a reflected wave signal of an ultrasound wave transmitted to an imaging target portion of a subject by using a reception delay time calculated from a set sound velocity set as a sound velocity in the imaging target portion. The image-creation control unit switches a set sound velocity set at a present moment in a variable range, and controls the image creating unit so as to create a plurality of ultrasound images each using a reception delay time corresponding to each of the set sound velocities to be switched. The display control unit controls display such that the ultrasound images created are displayed on a certain display unit.

18 Claims, 14 Drawing Sheets

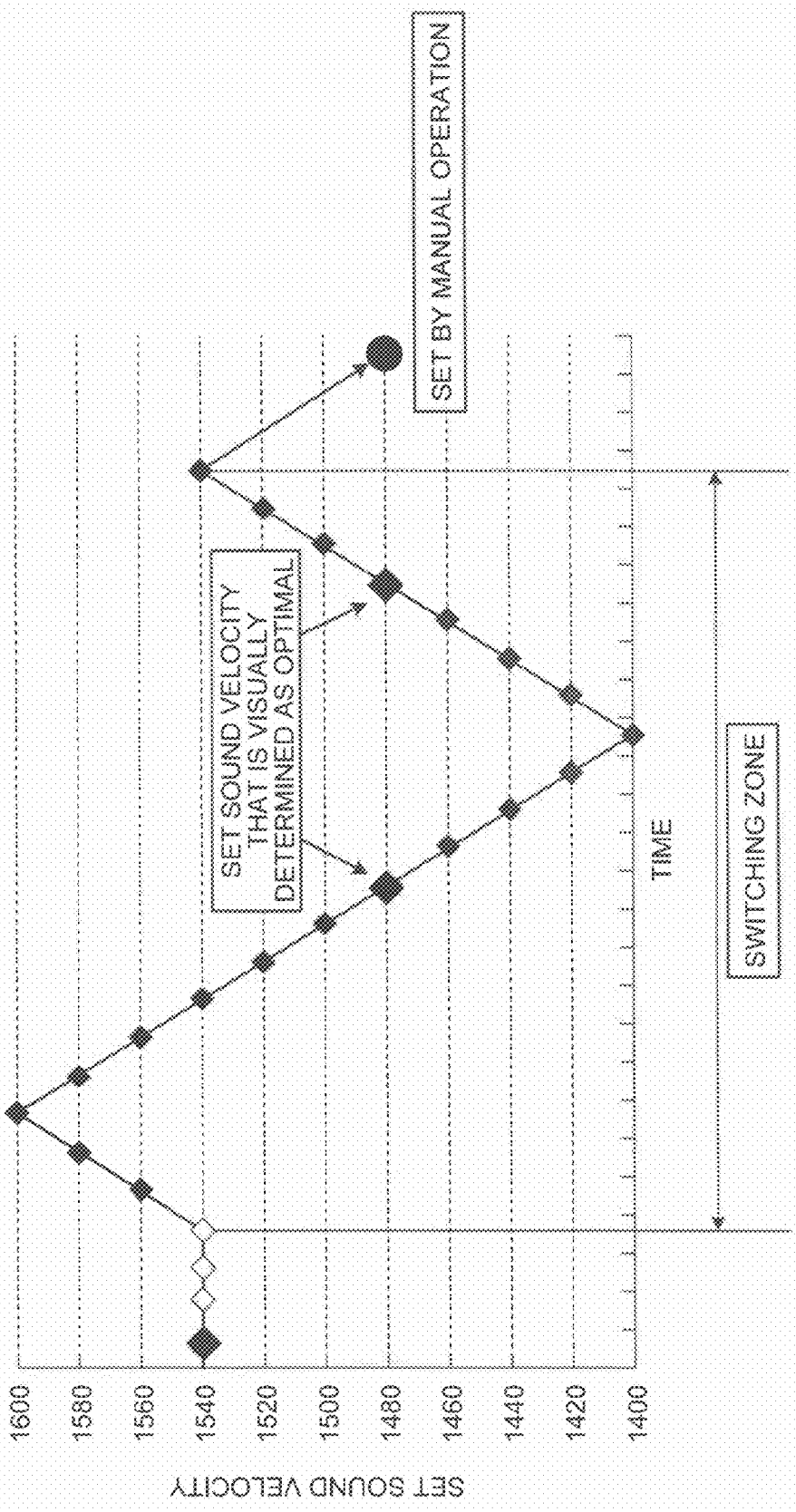

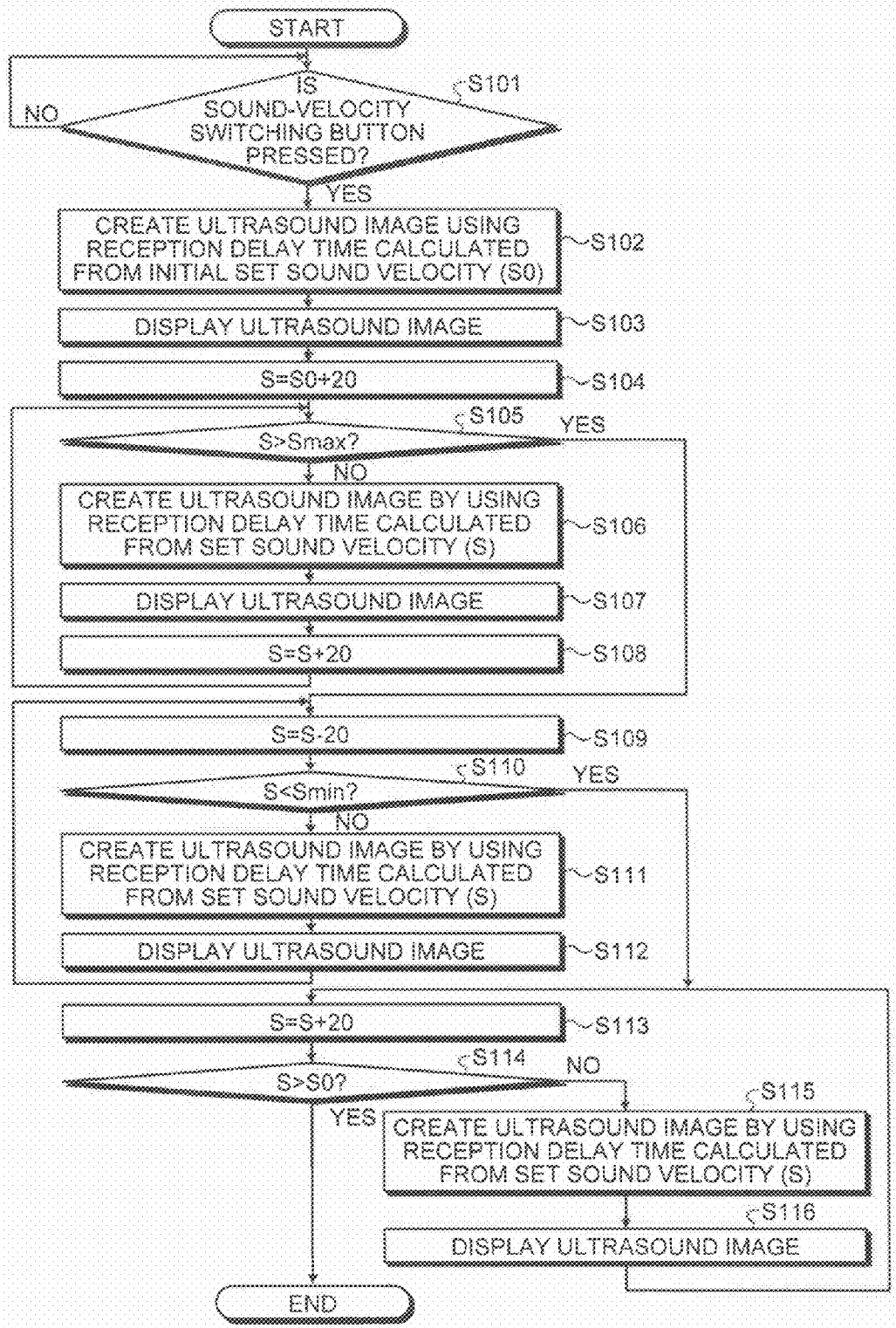

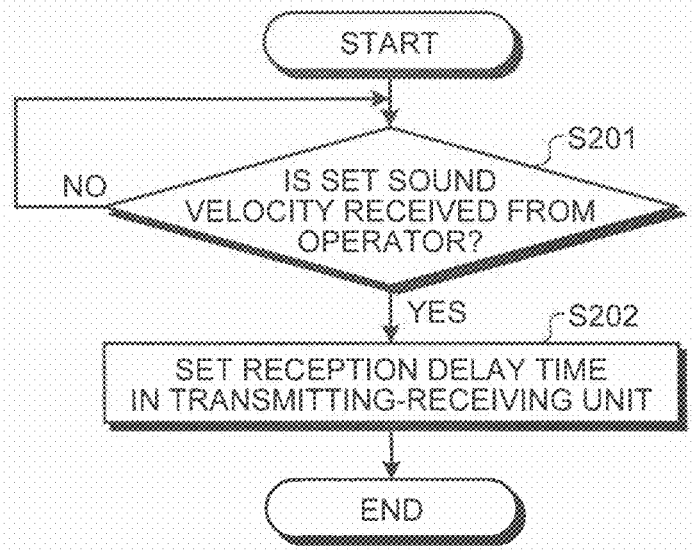
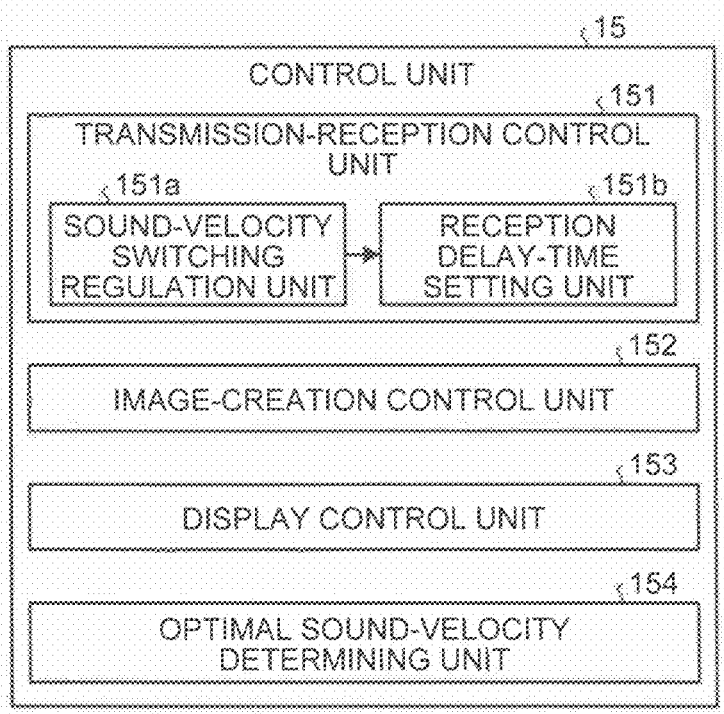

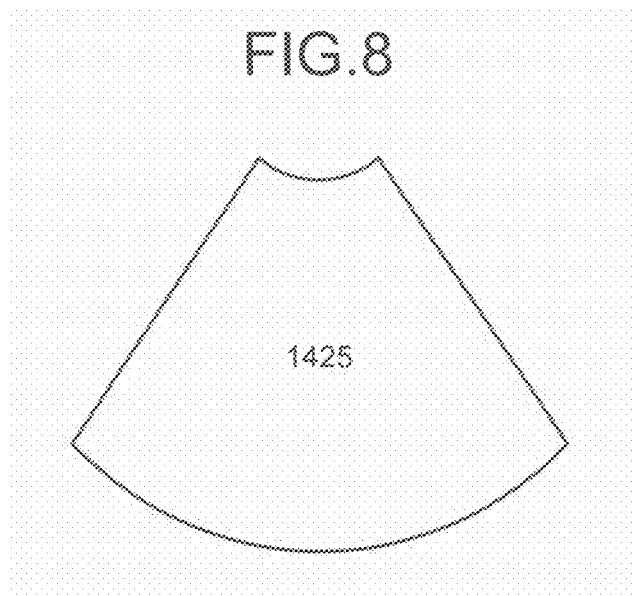

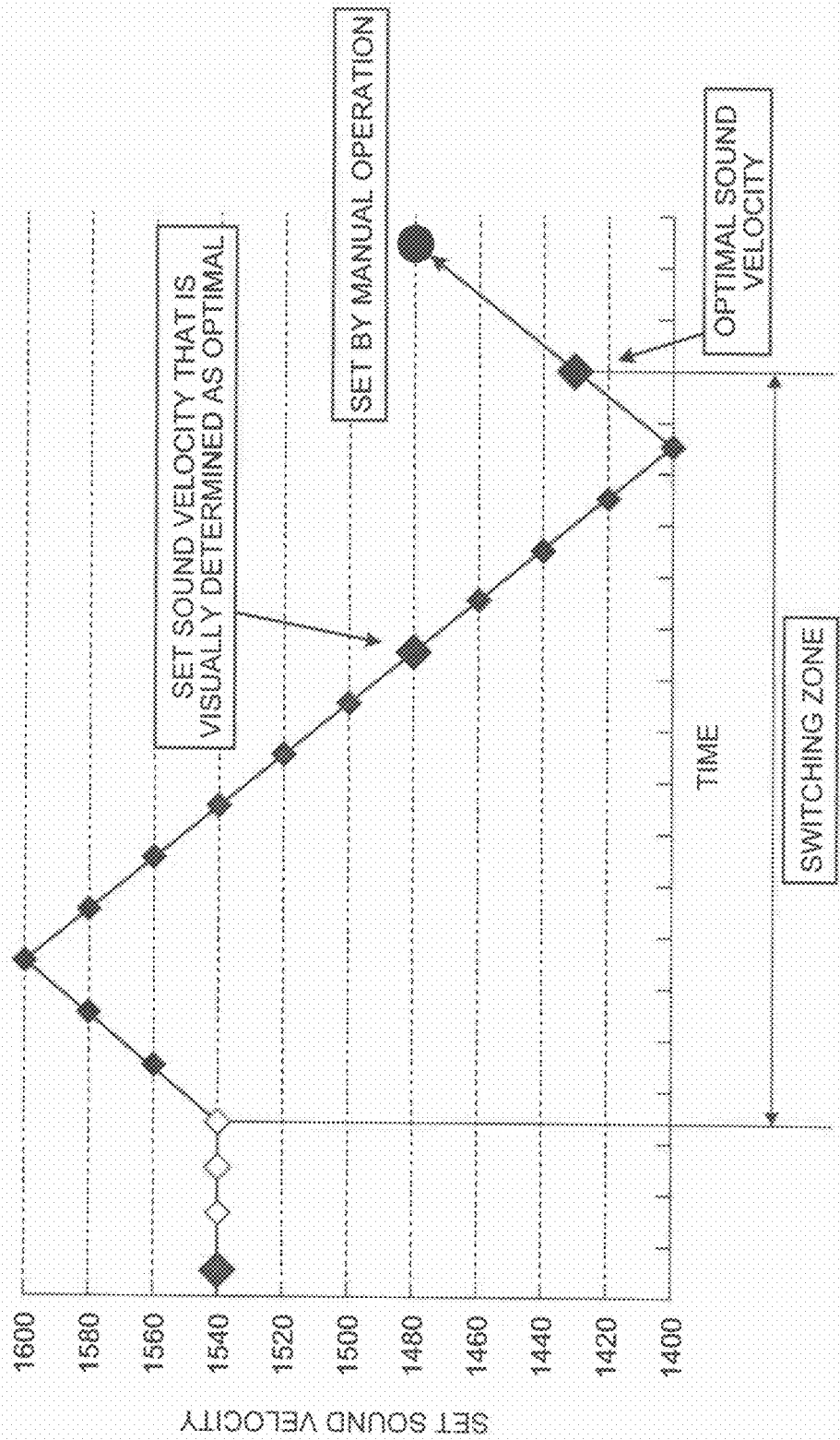

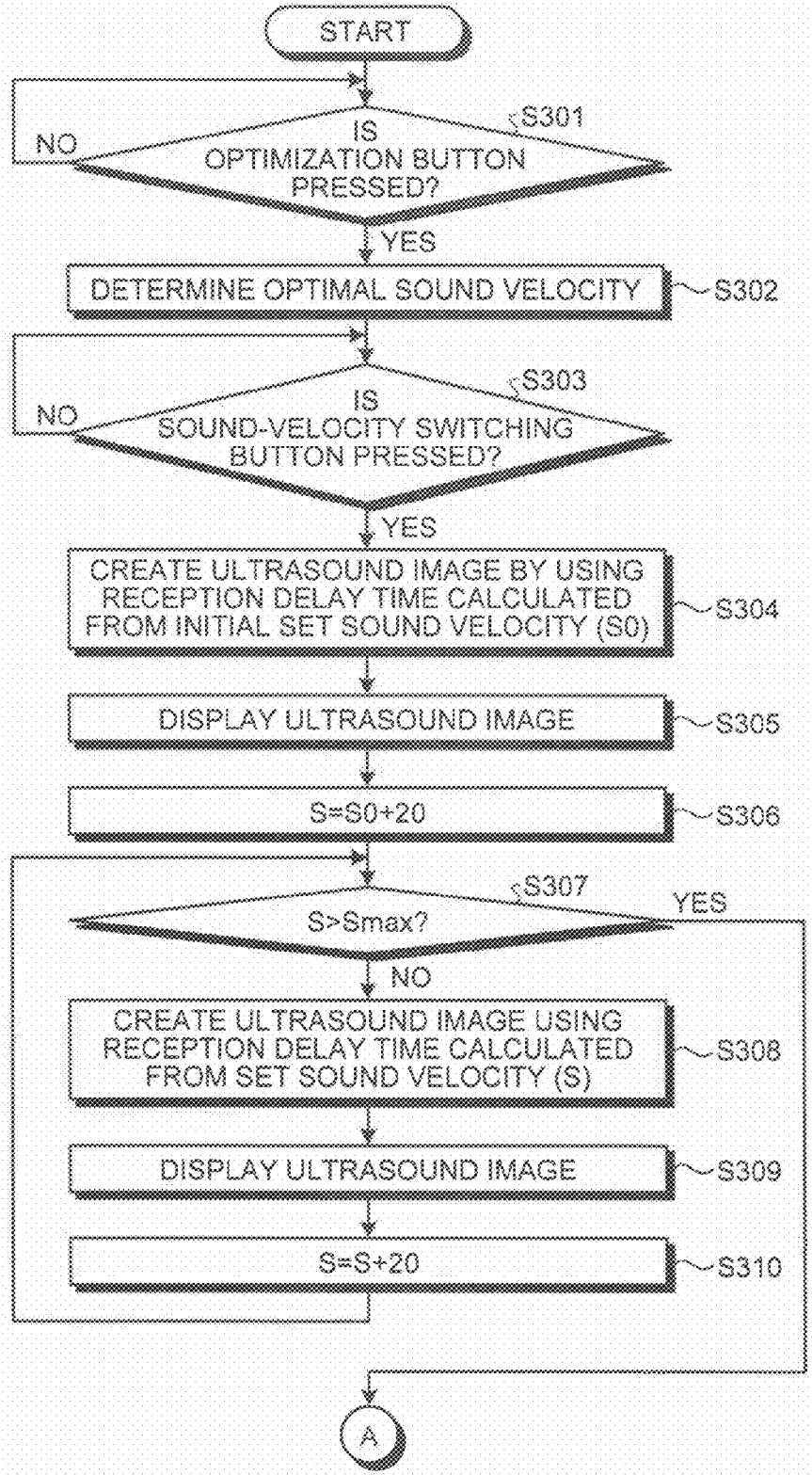

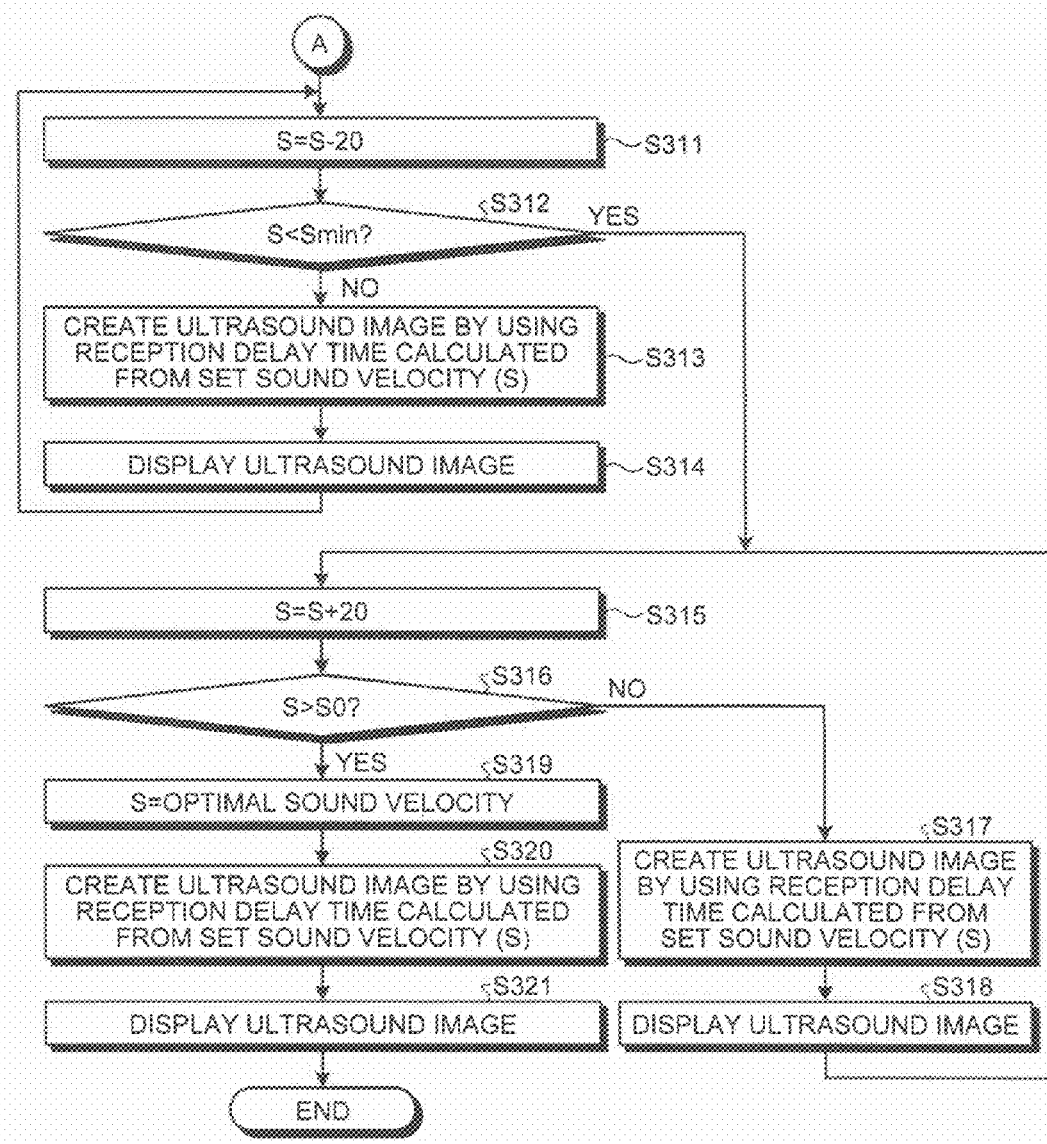

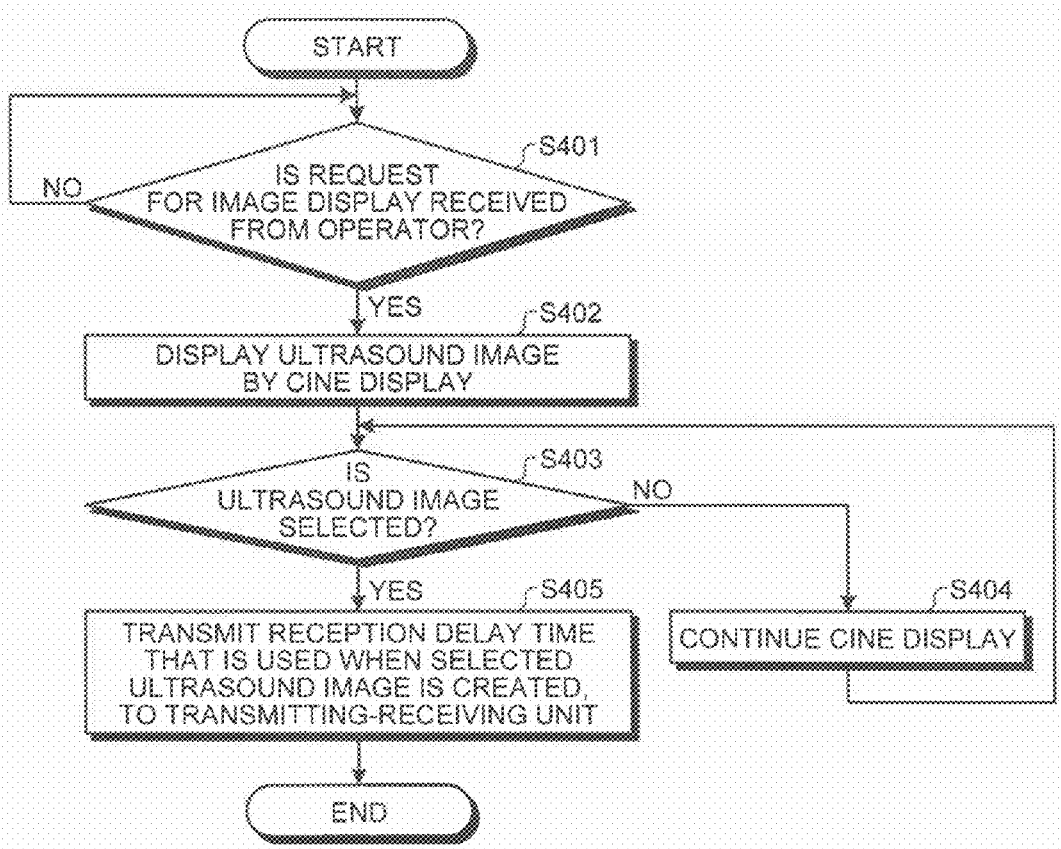

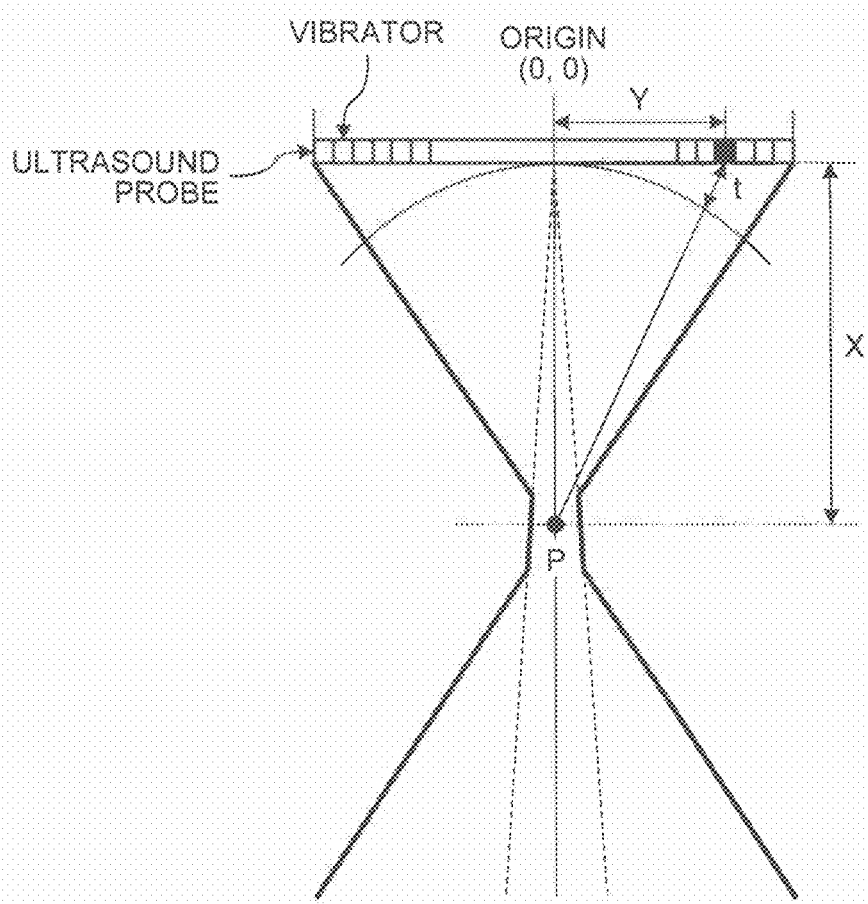

SET SOUND VELOCITY = BIO-SOUND-VELOCITY

SET SOUND VELOCITY < BIO-SOUND-VELOCITY

ULTRASOUND DIAGNOSIS APPARATUS AND METHOD OF SETTING SOUND VELOCITY

CROSS-REFERENCE TO RELATED APPLICATIONS

This application is based upon and claims the benefit of priority from Japanese Patent Application No. 2009-155477, filed on Jun. 30, 2009 and Japanese Patent Application No. 2010-116259, filed on May 20, 2010; the entire contents of all of which are incorporated herein by reference.

FIELD

Embodiments described herein relate generally to an ultrasound diagnosis apparatus and a method of setting sound velocity.

BACKGROUND

Conventionally, an ultrasound diagnosis apparatus employs a method of focusing a transmission beam and a reception beam of ultrasound waves in order to increase a lateral resolution of an ultrasound image. Particularly, an ultrasound diagnosis apparatus using an ultrasound probe including an array vibrator of an electronic scan type uses an electronic focusing method of adding reception signals of respective channels by delay-time control.

However, according to the electronic focusing method, a reception beam diffuses at a deep location distant from a focus point, consequently, a lateral resolution of an ultrasound image decreases. For this reason, a general ultrasound diagnosis apparatus uses a dynamic focusing method. The dynamic focusing method is a method of performing delay-time control such that a focus point continuously moves in a depth direction with time when receiving a reception beam, accordingly, a reception beam can be constantly obtained from a region a beam is focused.

The delay-time control according to the dynamic focusing method is explained below with reference to FIG. 13. FIG. 13 is a schematic diagram for explaining the delay-time control according to the dynamic focusing method.

The following description explains each position of an ultrasound-wave scanning plane by using a coordinate system having the origin at the center of an aperture of a vibrator present in a receiving aperture of an ultrasound probe, and including "a coordinate in a depth direction from the ultrasound probe", and "a coordinate in the traverse direction from the center of the aperture".

As shown in FIG. 13, when a focus point subjected to the delay-time control is a point positioned at coordinates (X, 0), a difference (delay time: Δt) between a time until a wavefront of a reflected sound wave generated at the focus point P reaches a vibrator positioned at coordinates (0, Y), and a time until the wavefront of the reflected sound wave generated at the focus point P reaches a vibrator positioned at the origin (0, 0) is defined by a difference (t) between distances of the focus point P and each vibrator. Such time difference is expressed by Expression (1) below. Where "C" described in Expression (1) denotes a sound velocity inside a medium subjected to ultrasound-wave scanning.

$$\Delta t = \frac{\sqrt{X^2 + Y^2} - X}{C} \quad (1)$$

According to the dynamic focus method, a delay time at each vibrator is calculated by using Expression (1), with respect to each of different focus points. Consequently, according to the dynamic focusing method, a delay time (reception delay time) when adding a signal (reception signal) of a reception beam received by each vibrator of an ultrasound probe is determined. Consequently, according to the dynamic focusing method, a distribution (delay distribution) that reception delay times of respective vibrators are determined is set at each focus point of the ultrasound-wave scanning plane. The ultrasound diagnosis apparatus that executes the dynamic focusing method focuses reception signals from respective focus points in different depth directions by adding them by using a reception delay time obtained from the delay distribution, thereby improving the lateral resolution of an ultrasound image.

The ultrasound diagnosis apparatus that executes the dynamic focusing method generally sets a delay distribution by assuming that a sound velocity "C" is a typical sound velocity of a diagnosis portion to be imaged. However, there is a report that sound velocity values inside a living body are different in portions (for example, "muscle: 1560 m/sec", and "fat: 1480 m/sec"). Moreover, there is a report that sound velocity values inside a living are different between subjects even in the same portion.

Therefore, when there is a difference between a sound velocity that is set (hereinafter, referred to as set sound velocity) and a sound velocity of a living body in a diagnosis portion (hereinafter, referred to as living-body sound velocity), a difference is produced between "a reception delay time for actually focusing a reception signal at a focus point" and "a reception delay time calculated by using Expression (1)". In other words, when there is a difference between a set sound velocity and a living-body sound velocity, a focus point for focusing a reception signal deviates, consequently, even by using the dynamic focusing method, the lateral resolution decreases and the image quality of an ultrasound image decreases.

For example, as shown in the left side of FIG. 14A, when the set sound velocity and the living-body sound velocity are equal, a focus point does not deviate at each position in different depth direction ($F_{n-1}$, $F_n$, $F_{n+1}$), so that the lateral resolution in each depth direction improves. For example, as shown in the right side of FIG. 14A, on an ultrasound image onto which a phantom is imaged, signals originating phantom are rendered as a point without blur.

However, as shown in the left side of FIG. 14B, for example, when a set sound velocity is smaller than a living-body sound velocity, a focus point deviates at each position in different depth direction ($F_{n-1}$, $F_n$, $F_{n+1}$), so that the lateral resolution in each depth direction decreases. For example, as shown in the right side of FIG. 14B, on an ultrasound image onto which a phantom is imaged, signals originating phantom blur in the traverse direction, so that the lateral resolution of the ultrasound image decreases. FIGS. 14A and 14B are schematic diagrams for explaining decrease in lateral resolution caused by a difference between a set sound velocity and a living-body sound velocity.

For this reason, in order to detect a living-body sound velocity in a diagnosis portion, technologies of such as a reflection method and a phase correction according to a cross-correlation method are known. However, according to such technologies, there are constraints that a reflective body, such as a calculus or a boundary wall, needs to be present in a detection area of a living-body sound velocity, and furthermore, a reflective body has to be a point, consequently, such technologies cannot be generally used.

Therefore, in order to calculate a reception delay time that guarantees the lateral resolution of an ultrasound image, a technology of optimizing a set sound velocity has been recently known (for example, see JP-A 2008-264531 (KOKAI)). Specifically, an ultrasound diagnosis apparatus creates a plurality of ultrasound images by using respective reception delay times that are calculated with different sound velocities. The ultrasound diagnosis apparatus then divides each ultrasound image into a plurality of small areas, and calculates a contrast value (for example, a variance of amplitude values) with respect to each of the small areas.

The ultrasound diagnosis apparatus then determines that an optimal sound velocity in each small area is a set sound velocity with which a contrast value is at the maximum, and uses the determined optimal sound velocity in each small area as the sound velocity (set sound velocity) when calculating a reception delay time in the corresponding small area. In other words, by determining an optimal sound velocity in each small area, the lateral resolution of an ultrasound image can be guaranteed.

However, according to the conventional technologies described above, although an optimal sound velocity in a particular area is determined with objective numerical values (contrast values); when the calculation precision of the contrast values is insufficient, there is a case where the lateral resolution of a portion to be focused by an engineer who takes an ultrasound image or an image reader who reads an ultrasound image does not always become optimal, even if the ultrasound image is created by the determined optimal sound velocity.

BRIEF DESCRIPTION OF THE DRAWINGS

FIG. 3 is a schematic diagram for explaining setting of sound velocity by an operator according to the first embodiment;

FIG. 4 is a flowchart for explaining ultrasound-image display processing by switching of set sound velocity of the ultrasound diagnosis apparatus according to the first embodiment;

FIG. 5 is a flowchart for explaining reception delay-time setting processing of the ultrasound diagnosis apparatus according to the first embodiment;

FIG. 6 is a schematic diagram for explaining a configuration of a control unit according to a second embodiment;

FIGS. 7A, 7B, and 8 are schematic diagrams for explaining an optimal sound-velocity determining unit;

FIG. 9 is a schematic diagram for explaining setting of a sound velocity by an operator according to the second embodiment;

FIGS. 10A and 10B are flowcharts for explaining ultrasound-image display processing by switching of set sound velocity of an ultrasound diagnosis apparatus according to the second embodiment;

FIG. 11 is a flowchart for explaining reception delay-time setting processing of an ultrasound diagnosis apparatus according to a third embodiment;

FIG. 13 is a schematic diagram for explaining delay-time control according to a dynamic focusing method.

DETAILED DESCRIPTION

In one embodiment, an ultrasonic diagnostic apparatus includes an image creating unit, an image-creation control unit and a display control unit. The image creating unit creates an ultrasound image from data created by adding a reflected wave signal of an ultrasound wave transmitted to an imaging target portion of a subject by using a reception delay time calculated from a set sound velocity set as a sound velocity in the imaging target portion. The image-creation control unit switches a set sound velocity set at a present moment in a variable range in which the ultrasound diagnosis apparatus can variably set set sound velocities, based on an instruction from an operator received via a certain input unit, and controls the image creating unit so as to create a plurality of ultrasound images each using a reception delay time corresponding to each of the set sound velocities to be switched. The display control unit controls display such that the ultrasound images created by the control by the image-creation control unit are displayed on a certain display unit.

Exemplary embodiments of an ultrasound diagnosis apparatus and a method of setting sound velocity will be explained below in detail with reference to the accompanying drawings. An ultrasound diagnosis apparatus that executes a method of setting sound velocity is explained below as the embodiments.

Figure 1:
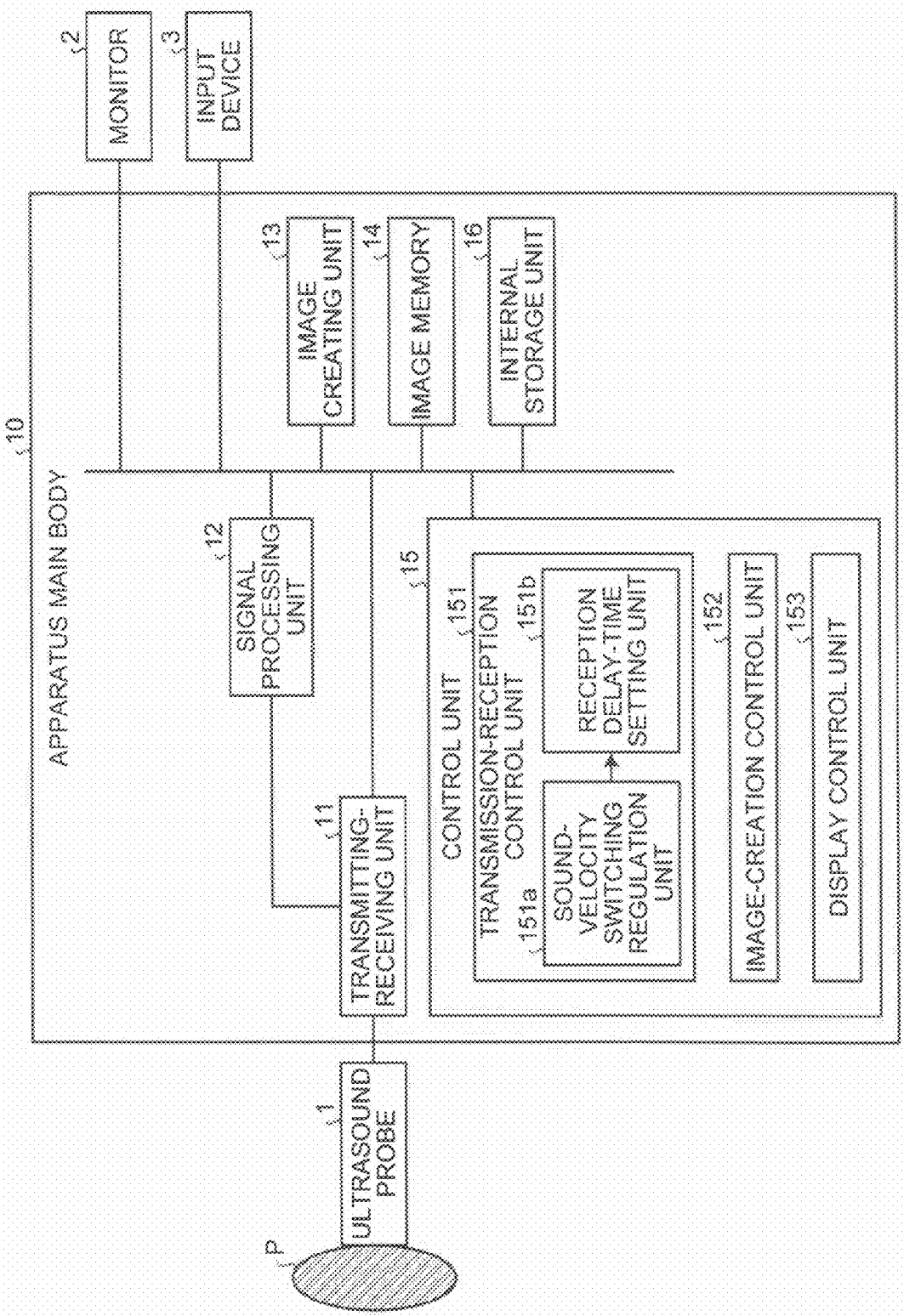
FIG. 1 is a schematic diagram for explaining a configuration of an ultrasound diagnosis apparatus according to a first embodiment.

First of all, a configuration of an ultrasound diagnosis apparatus according to an embodiment is explained below. FIG. 1 is a schematic diagram for explaining a configuration of an ultrasound diagnosis apparatus according to a first embodiment. As shown in FIG. 1, the ultrasound diagnosis apparatus according to the embodiment includes an ultrasound probe 1, a monitor 2, an input device 3, and an apparatus main body 10.

The ultrasound probe 1 includes a plurality of piezoelectric vibrators of an electronic scan type that are arranged on a row. The piezoelectric vibrators generate ultrasound waves based on a driving signal supplied from a transmitting-receiving unit 11 included in the apparatus main body 10, which will be described later. Furthermore, the piezoelectric vibrators receive a reflected wave from a subject P, and convert it into an electric signal. Moreover, the ultrasound probe 1 includes a conformation layer provided to the piezoelectric vibrators, and a backing material that prevents propagation of an ultrasound wave backward from the piezoelectric vibrators.

When an ultrasound wave is transmitted from the ultrasound probe 1 to the subject P, the transmitted ultrasound wave is reflected consecutively by discontinuity planes of acoustic impedance in internal body tissue of the subject P, and received by the piezoelectric vibrators included in the ultrasound probe 1 as a reflected wave signal. The amplitude of the received reflected wave signal depends on a difference in the acoustic impedance of the discontinuity planes that reflect the ultrasound wave. A reflected wave signal that a transmitted ultrasound pulse is reflected by a moving blood flow or a surface of a heart wall is dependent on a velocity component in the ultrasound-wave transmitting direction of a moving body due to the Doppler effect, and is affected by a frequency deviation.

The input device 3 includes a mouse, a keyboard, a button, a panel switch, a touch command screen, a foot switch, a trackball, and the like. The input device 3 receives various setting requests from an operator of the ultrasound diagnosis apparatus, and transfers each of the received various setting requests to the apparatus main body 10. The various setting requests received by the input device 3 from the operator will be explained later in detail.

The monitor 2 displays a Graphical User Interface (GUI) for an operator of the ultrasound diagnosis apparatus to input various setting requests by using the input device 3, and displays an ultrasound image created by the apparatus main body 10.

The apparatus main body 10 is a device that creates an ultrasound image based on a reflected wave signal received by the ultrasound probe 1; and includes the transmitting-receiving unit 11, a signal processing unit 12, an image creating unit 13, an image memory 14, a control unit 15, and an internal storage unit 16, as shown in FIG. 1.

The transmitting-receiving unit 11 controls transmission directivity and reception directivity in transmission and reception of ultrasound waves performed by the ultrasound probe 1. Specifically, the transmitting-receiving unit 11 includes a trigger generating circuit, a delay circuit, a pulsar circuit, and the like; and supplies a driving signal to the ultrasound probe 1. The pulsar circuit repeatedly generates a rate pulse for forming a transmission ultrasound wave at a certain rate frequency. The delay circuit gives to each rate pulse generated by the pulsar circuit, a delay time per piezoelectric vibrator required for focusing an ultrasound wave generated from the ultrasound probe 1 into a beam and determining transmission directivity. The trigger generating circuit applies a driving signal (driving pulse) to the ultrasound probe 1 at timing based on the rate pulse. In other words, the delay circuit focuses an ultrasound beam transmitted from the piezoelectric vibrator plane by changing the delay time given to each rate pulse, and then arbitrarily adjusts the transmitting direction of the ultrasound beam.

Moreover, the transmitting-receiving unit 11 includes an amplifier circuit, an analog/digital (A/D) converter, an adder, and the like; and performs various processing on a reflected wave signal received by the ultrasound probe 1, thereby creating reflected wave data. The amplifier circuit amplifies a reflected wave signal in each channel, thereby performing gain correction processing. The A/D converter converts from analog to digital the reflected wave signal of which gain is corrected, and gives a delay time required for determining reception directivity. The adder performs addition processing of the reflected wave signals processed by the A/D converter, thereby creating reflected wave data.

Specifically, the A/D converter gives the adder a distribution of reception delay times each of which is calculated with respect to each focus point on an ultrasound-wave scanning plane, based on a set sound velocity that is preliminarily set as a sound velocity of internal body tissue of the subject P to be imaged onto an ultrasound image. The adder then performs delay-time control such that focus points move continuously in a depth direction as time elapses, based on the distribution of the reception delay times given by the A/D converter, thereby performing addition processing of reflected wave signals from a focused region. Owing to the addition processing by the adder, a reflected component from a direction in accordance with the reception directivity of a reflected wave signal is enhanced. A set sound velocity is set by the operator to a value that is the sound velocity inside an imaging target portion, within a variable range that can be variably set in the ultrasound diagnosis apparatus.

Precisely, the ultrasound diagnosis apparatus according to the embodiment adds reflected wave signals by using a reception delay time calculated from a set sound velocity by the transmitting-receiving unit 11, so as not to decrease the lateral resolution of an ultrasound image, thereby executing a dynamic focusing method of creating reflected wave data.

The transmitting-receiving unit 11 has a function by which delay information, a transmission frequency, a transmission driving voltage, the number of opening elements, and the like, can be instantly changed by the control by the control unit 15, which will be described later. Furthermore, the transmitting-receiving unit 11 can transmit and receive a different wave form with respect to each frame or each rate.

The signal processing unit 12 receives from the transmitting-receiving unit 11 reflected wave data that is a processed reflected wave signal on which the gain correction processing, the A/D conversion processing, and the addition processing are performed. The signal processing unit 12 then performs logarithmic amplification, envelope detection processing, and the like, thereby creating data that a signal strength is expressed in brightness (B-mode data).

Moreover, the signal processing unit 12 performs a frequency analysis on velocity information from the reflected wave data received from the transmitting-receiving unit 11, and extracts echo components of a blood flow, tissue, and a contrast agent owing to the Doppler effect, thereby creating data (doppler data) that moving body information, such as an average velocity, a distribution, and a power, is extracted with respect to a number of points.

The image creating unit 13 processes the B-mode data created by the signal processing unit 12, thereby creating a B-mode image on which the strength of a reflected wave is expressed in brightness, as an ultrasound image for display. Moreover, as an ultrasound image for display, the image creating unit 13 creates a doppler image as an average velocity image, a distribution image, a power image, or a combination image of them, each of which indicates moving body information in an imaging target portion, for example, information about a blood flow, from the doppler data created by the signal processing unit 12.

The image memory 14 is a memory that stores the B-mode data and the doppler data created by the signal processing unit 12, and the B-mode image and the doppler image created by the image creating unit 13. Moreover, the image memory 14 can store image data in parallel that is obtained under different transmission and reception conditions; and after imaging, the operator can access an image recorded during the imaging.

The control unit 15 controls the whole processing performed by the ultrasound diagnosis apparatus. Specifically, the control unit 15 controls processing performed by the transmitting-receiving unit 11, the signal processing unit 12, and the image creating unit 13, and controls display such that an ultrasound image stored by the image memory 14 is to be displayed on the monitor 2, based on various setting requests input by the operator via the input device 3, and various control programs read from the internal storage unit 16, which will be described later. Control processing performed by the control unit 15 according to the embodiment will be explained later.

The internal storage unit 16 stores various data, such as control programs for performing ultrasound-wave transmission and reception, image creation processing, and display processing; diagnosis information (for example, a patient identification (ID), a doctor's comment, and the like); a diagnosis protocol, and various body marks. Moreover, the internal storage unit 16 is used for storing an image stored by the image memory 14, as required. Data stored by the internal storage unit 16 can be transferred to an external peripheral device via a not-shown interface circuit.

In this way, the ultrasound diagnosis apparatus according to the first embodiment creates reflected wave data by adding reflected wave signals of ultrasound waves transmitted onto an imaging target portion of the subject P by using a reception delay time calculated from a set sound velocity that is set as a sound velocity inside the imaging target portion, by the dynamic focusing method; and then creates an ultrasound image from the created reflected wave data.

Figure 2:
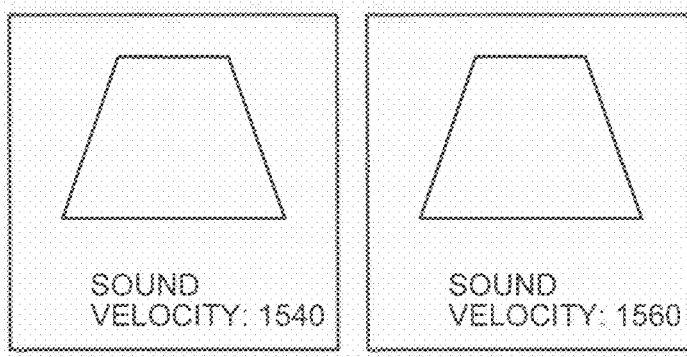
FIG. 2 is a schematic diagram for explaining an example of ultrasound images that are sequentially displayed by a display control unit.

As the control processing by the control unit 15, which will be described below in detail, is then executed, the ultrasound diagnosis apparatus according to the first embodiment can optimize the lateral resolution of a portion to be focused on an ultrasound image by an operator or an interpreter. Control processing by the control unit 15 is explained below with reference to FIGS. 1, 2 and 3. FIG. 2 is a schematic diagram for explaining an example of ultrasound images that are sequentially displayed by a display control unit; and FIG. 3 is a schematic diagram for explaining setting of sound velocity by an operator according to the first embodiment.

As shown in FIG. 1, the control unit 15 according to the first embodiment includes a transmission-reception control unit 151, an image-creation control unit 152, and a display control unit 153.

The transmission-reception control unit 151 includes a sound-velocity switching regulation unit 151a, and a reception delay-time setting unit 151b. After the ultrasound probe 1 transmits an ultrasound beam, and an imaging target portion of the subject P becomes ready to be scanned, and then when a sound-velocity switching button included in the input device 3 is pressed by the operator, the sound-velocity switching regulation unit 151a regulates the set sound velocity set at the present moment in the ultrasound diagnosis apparatus so as to switch sequentially within the variable range described above.

The reception delay-time setting unit 151b calculates a reception delay time corresponding to each of a plurality of set sound velocities that are regulated to be sequentially switched by the sound-velocity switching regulation unit 151a, and sequentially transmits the calculated reception delay time to the transmitting-receiving unit 11.

The image-creation control unit 152 controls the adder of the transmitting-receiving unit 11 so as to create reflected wave data sequentially through addition processing using a received reception delay time, each time when a reception delay time corresponding to each of a plurality of set sound velocities is sequentially transmitted from the transmission-reception control unit 151 to the transmitting-receiving unit 11 as the sound-velocity switching button is pressed by the operator.

The image-creation control unit 152 then controls the signal processing unit 12 so as to create B-mode data sequentially each time when the reflected wave data is received from the transmitting-receiving unit 11.

The image-creation control unit 152 then controls the image creating unit 13 so as to create an ultrasound image of a B-mode image each time when the B-mode data is sequentially received from the signal processing unit 12.

The display control unit 153 controls display so as to display on the monitor 2 a plurality of ultrasound images of respective different set sound velocities that is sequentially created by the image creating unit 13 by the control by the image-creation control unit 152.

For example, as shown in FIG. 2, the display control unit 153 performs control so as to display set sound velocities (1540 m/sec, and 1560 m/sec) used for creation of each of a plurality of ultrasound images on the monitor 2 together with the ultrasound images.

Accordingly, the operator continuously refers to the ultrasound images sequentially created with the respective different set sound velocities (reception delay times), thereby being able to determine a set sound velocity of an ultrasound image of which the lateral resolution becomes optimal in a portion to be focused. A concrete example of a series of processing described above is explained below with reference to FIG. 3.

For example, as shown in FIG. 3, assuming that the set sound velocity at the present moment is "1540 m/sec", and a variable range of the set sound velocity is "from 1400 m/sec to 1600 m/sec"; when the sound-velocity switching button is pressed, the sound-velocity switching regulation unit 151a regulates switching of the set sound velocity based on that time-intervals of switching the sound velocity are regular, and value-intervals of switching the sound velocity value are constant (interval 20 m/sec in the figure).

In other words, as shown in FIG. 3, the sound-velocity switching regulation unit 151a regulates the switching of the set sound velocity through a switching route that: the set sound velocity is increased by the interval 20 m/sec from "1540 m/sec" to "1600 m/sec" at regular time-intervals; the set sound velocity is decreased by the interval 20 m/sec from "1600 m/sec" to "1400 m/sec" at regular time-intervals; and furthermore, the set sound velocity is increased by the interval 20 m/sec from "1400 m/sec" to "1540 m/sec" at regular time-intervals.

The sound-velocity switching regulation unit 151a regulates a zone (switching zone) in which the set sound velocity is automatically switched by regulating the time-intervals of switching the sound velocity and the value-intervals of switching the sound velocity value, as shown in FIG. 3.

The operator then refers to ultrasound images sequentially displayed on the monitor 2 in the switching zone, and visually determines the set sound velocity of an ultrasound image of which the lateral resolution of a portion to be focused becomes optimal. The operator then sets the value of a set sound velocity (1480 m/sec) that is visually determined as optimal, manually with the keyboard of the input device 3, for example, as shown in FIG. 3.

When the set sound velocity is received from the operator via the input device 3, the image-creation control unit 152 sets a reception delay time calculated by the reception delay-time setting unit 151b by using the received set sound velocity, into the transmitting-receiving unit 11. Accordingly, the signal processing unit 12 and the image creating unit 13 create ultrasound images using the reception delay time corresponding to the set sound velocity that is determined as optimal by the operator, and the created ultrasound images are displayed on the monitor 2 by the control by the display control unit 153.

Processing by the ultrasound diagnosis apparatus according to the first embodiment is explained below with reference to FIGS. 4 and 5. FIG. 4 is a flowchart for explaining ultrasound-image display processing by switching of set sound velocity of the ultrasound diagnosis apparatus according to the first embodiment; FIG. 5 is a flowchart for explaining reception delay-time setting processing of the ultrasound diagnosis apparatus according to the first embodiment.

As shown in FIG. 4, according to the ultrasound diagnosis apparatus of the first embodiment; after the ultrasound probe 1 transmits an ultrasound beam, and an imaging target portion of the subject P becomes ready to be scanned, and then when the sound-velocity switching button of the input device 3 is pressed by the operator (Yes at Step S101); by the control by the image-creation control unit 152, the image creating unit 13 creates an ultrasound image using a reception delay time calculated from an initial set sound velocity (S0) that is the set sound velocity at the present moment (Step S102).

In other words, by the control by the image-creation control unit 152, the transmitting-receiving unit 11 creates reflected wave data by using a reception delay time corresponding to an initial set sound velocity; the signal processing unit 12 creates B-mode data by using the reflected wave data received from the transmitting-receiving unit 11; and the image creating unit 13 creates an ultrasound image from the B-mode data received from the signal processing unit 12.

The monitor 2 then displays the ultrasound image created at Step S102, by the control by the display control unit 153 (Step S103).

Subsequently, if a value-interval of switching the sound velocity value is an "interval 20 m/sec", the sound-velocity switching regulation unit 151a calculates a set sound velocity "S" at "S=S0+20"(Step S104); and determines whether the calculated "S" is a larger value than "Smax" that is the maximum value in a variable zone (Step S105).

If the calculated "S" is equal to or smaller than "Smax" that is the maximum value in the variable zone (No at Step S105); by the control by the image-creation control unit 152, the image creating unit 13 creates an ultrasound image by using a reception delay time calculated from the set sound velocity (S) (Step S106).

In other words, when the sound-velocity switching regulation unit 151a determines that "S" is equal to or smaller than "Smax", the reception delay-time setting unit 151b sets the reception delay time calculated from "S" in the transmitting-receiving unit 11. By the control by the image-creation control unit 152, the transmitting-receiving unit 11 then creates reflected wave data by using the reception delay time set by the reception delay-time setting unit 151b; the signal processing unit 12 creates B-mode data by using the reflected wave data received from the transmitting-receiving unit 11; and the image creating unit 13 creates an ultrasound image from the B-mode data received from the signal processing unit 12.

The monitor 2 then displays the ultrasound image created at Step S106, by the control by the display control unit 153 (Step S107).

After that, the sound-velocity switching regulation unit 151a renews the set sound velocity (S) to be set next to "S=S+20" (Step S108); returns to Step S105, and determines whether the renewed "S" is a larger value than "Smax".

By contrast, if "S" calculated at Step S104 or Step S108 is a larger value than "Smax" (Yes at Step S105); the sound-velocity switching regulation unit 151a renews the set sound velocity (S) to be set next to "S=S−20" (Step S109); and determines whether the renewed "S" is a smaller value than "Smin" that is the minimum value in the variable zone (Step S110).

If the calculated "S" is equal to or larger than "Smin" (No at Step S110); by the control by the image-creation control unit 152, the image creating unit 13 creates an ultrasound image by using a reception delay time calculated from the set sound velocity (S) (Step S111); and the monitor 2 displays the ultrasound image created at Step S111, by the control by the display control unit 153 (Step S112).

The sound-velocity switching regulation unit 151a then returns to Step S109 and renews the set sound velocity (S) to be set next to "S=S−20", and determines whether the renewed "S" is a smaller value than "Smin" that is the minimum value in the variable zone at Step S110.

By contrast, if "S" calculated at Step S109 is a smaller value than "Smin" (Yes at Step S110); the sound-velocity switching regulation unit 151a renews the set sound velocity (S) to be set next to "S=S+20" (Step S113); and determines whether the renewed "S" is a larger value than "S0" (Step S114).

If the renewed (S) is equal to or smaller than "S0" (No at Step S114); by the control by the image-creation control unit 152, the image creating unit 13 creates an ultrasound image by using a reception delay time calculated from the set sound velocity (S) (Step S115); and the monitor 2 displays the ultrasound image created at Step S111, by the control by the display control unit 153 (Step S116).

By contrast, if the renewed (S) is a larger value than "S0" (Yes at Step S114); the sound-velocity switching regulation unit 151a counts the switching zone as ended, and terminates the processing.

As shown in FIG. 5, when a set sound velocity is then received from the operator who refers to the ultrasound images sequentially displayed by the monitor 2 in accordance with the flowchart shown in FIG. 4 (Yes at Step S201); the reception delay-time setting unit 151b calculates a reception delay time from the received set sound velocity, and sets the calculated reception delay time in the transmitting-receiving unit 11 (Step S202); and the processing is terminated. After that, by the control by the image-creation control unit 152, the image creating unit 13 creates an ultrasound image using the reception delay time corresponding to the set sound velocity determined as optimal by the operator.

As described above, according to the first embodiment, the sound-velocity switching regulation unit 151a regulates the set sound velocity set at the present moment so as to switch sequentially within the variable range. The reception delay-time setting unit 151b calculates a reception delay times corresponding to each of a plurality of set sound velocities that are regulated to be sequentially switched by the sound-velocity switching regulation unit 151a, and sequentially transmits the calculated reception delay time to the transmitting-receiving unit 11.

The image-creation control unit 152 controls the adder of the transmitting-receiving unit 11 so as to create reflected wave data sequentially through addition processing using a received reception delay time, each time when a reception delay time is sequentially transmitted from the reception delay-time setting unit 151b to the transmitting-receiving unit 11. The image-creation control unit 152 then controls the signal processing unit 12 so as to create B-mode data sequentially each time when the reflected wave data is received from the transmitting-receiving unit 11, and controls the image creating unit 13 so as to create an ultrasound image of a B-mode image each time when the B-mode data is sequentially received from the signal processing unit 12. The display control unit 153 controls display so as to display on the monitor 2 sequentially a plurality of ultrasound images of respective different set sound velocities that is sequentially created by the image creating unit 13 by the control by the image-creation control unit 152.

Consequently, according to the first embodiment, the operator can determine a sound velocity with which the lateral resolution in a portion to be focused becomes optimal by actually referring to it, and the lateral resolution of the portion to be focused on an ultrasound image can be optimized. In other words, according to the first embodiment, control of a reception focus to be determined by a sound velocity can be performed with a sound velocity determined as optimal by the operator.

Moreover, according to the first embodiment, when displaying sequentially-created ultrasound images sequentially on the monitor 2, the display control unit 153 controls display such that sound velocities used for creating respective ultrasound images are also displayed together. Therefore, according to the first embodiment, the operator can easily grasp and set a sound velocity with which the lateral resolution of a portion to be focused becomes optimal.

The above description is explained in a case where a sound velocity determined as optimal by an operator who refers to sound velocities displayed together with ultrasound images is set. However, the embodiment can be in a case where a value displayed together with each ultrasound image is an index value that relatively indicates a set sound velocity used for creating the ultrasound image, instead of the set sound velocity itself. Such index value can be such that assuming the set sound velocity at the present moment is "0", the value increases and decreases to, for example, "−1", "+2", "−1", or "−2", in accordance with increase and decrease in the set sound velocity. When index values are displayed together with ultrasound images, the operator sets an index value that the operator determines as optimal. Also in such case, the operator can easily grasp and set an index value with which the lateral resolution of a portion to be focused becomes optimal. The reception delay-time setting unit 151b calculates a reception delay time by using a sound velocity corresponding to a received index value.

Moreover, according to the embodiment is explained below in a case where as a set sound velocity or an index value displayed together with an ultrasound image is set by an operator, a reception delay time for creating an ultrasound image in an imaging target portion is set. However, the embodiment is not limited to this, and can be in a case where an operator who refers to ultrasound images displayed during a switching zone presses a freeze button of the input device 3 at the moment when an ultrasound image determined as optimal is displayed, so that a reception delay time used for creating the ultrasound image displayed at the moment when the freeze button is pressed is set as a reception delay time for creating an ultrasound image of the imaging target portion.

Accordingly, the operator can create an ultrasound image using a reception delay time calculated from the set sound velocity determined as optimal by the operator only by operating the input device 3, thereby being able to refer to an ultrasound image of which the lateral resolution in a portion to be focused on the ultrasound image becomes optimal, easily.

Figure 7A:
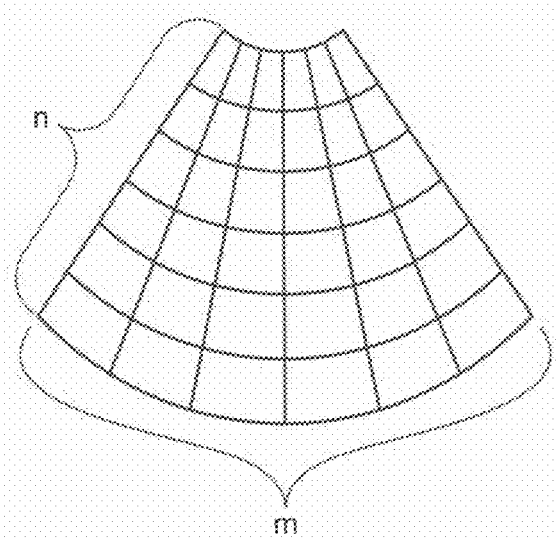
Figure 7B:
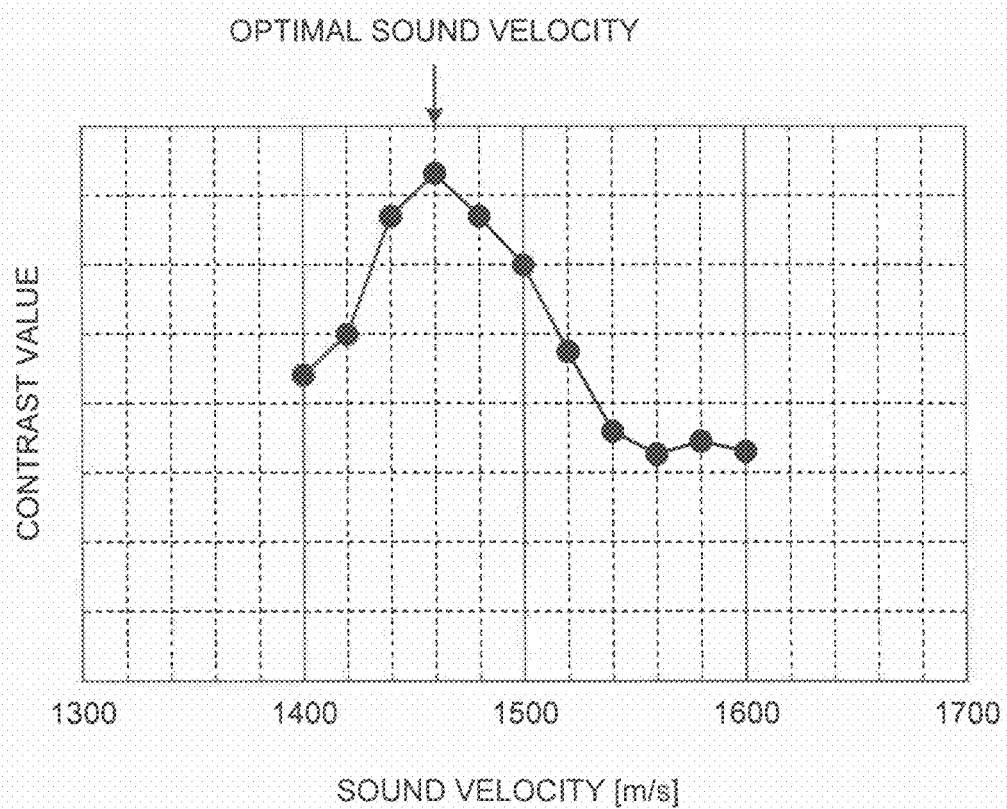

A second embodiment is explained in a case where a sound velocity with which the lateral resolution of an ultrasound image becomes optimal is automatically determined, and then the processing according to the first embodiment described above is executed, with reference to FIGS. 6 to 9. FIG. 6 is a schematic diagram for explaining a configuration of a control unit according to the second embodiment; FIGS. 7A, 7B, and 8 are schematic diagrams for explaining an optimal sound-velocity determining unit; and FIG. 9 is a schematic diagram for explaining setting of a sound velocity by an operator according to the second embodiment.

An ultrasound diagnosis apparatus according to the second embodiment is different as shown in FIG. 6, with respect to a point that the control unit 15 newly includes an optimal sound-velocity determining unit 154, compared with the ultrasound diagnosis apparatus according to the first embodiment explained above with reference FIG. 1. The following description mainly explains this.

The optimal sound-velocity determining unit 154 calculates a contrast value between each of a plurality of ultrasound images of an imaging target portion of the subject P that is preliminarily created by using a plurality of reception delay times calculated from a plurality of different set sound velocities. The optimal sound-velocity determining unit 154 then determines that an optimal sound velocity is a set sound velocity corresponding to an ultrasound image of which calculated contrast value becomes optimal.

Processing by the optimal sound-velocity determining unit 154 is started as an optimization button included in the input device 3 is pressed by the operator. Specifically, after the ultrasound probe 1 transmits an ultrasound beam, and an imaging target portion of the subject P becomes ready to be scanned, and then when the optimization button is pressed; for example, similarly to the first embodiment, by the control by the transmission-reception control unit 151, reception delay times calculated from set sound velocities sequentially regulated in a variable range are set in the transmitting-receiving unit 11; and the signal processing unit 12 and the image creating unit 13 create a plurality of ultrasound images by the control by the image-creation control unit 152.

The optimal sound-velocity determining unit 154 then calculates a contrast value between each of the ultrasound images that are created as the optimization is pressed. Specifically, as shown in FIG. 7A, the optimal sound-velocity determining unit 154 divides an ultrasound image into small areas, "n" sections along an ultrasound beam transmission direction, and "m" sections along an arrangement direction of the piezoelectric vibrators, and calculates a contrast value (for example, a variance of amplitudes) between the same small areas of each of the ultrasound images.

The optimal sound-velocity determining unit 154 then determines an optimal sound velocity in each small area. For example, as shown in FIG. 7B, the optimal sound-velocity determining unit 154 creates a graph on which contrast values calculated on a corresponding ultrasound image are plotted for each small area, with respect to sound velocities used in the same small area for creating ultrasound images. The optimal sound-velocity determining unit 154 then determines that the optimal sound velocity in a corresponding small area is a sound velocity with which a contrast value is at the maximum, as shown in FIG. 7B.

The optimal sound-velocity determining unit 154 then determines an optimal sound velocity in each small area; and for example, as shown in FIG. 8, calculates an average value from all of the determined optimal sound velocities in respective small areas, and determines that the calculated average value (1425 m/sec) is the optimal sound velocity for calculating a reception delay time in the imaging target portion of the subject P.

After the optimal sound-velocity determining unit 154 determines the optimal sound velocity, in order to determine whether the optimal sound velocity determined by the optimal sound-velocity determining unit 154 is a sound velocity that actually optimizes the lateral resolution of the portion to be focused by the operator on an ultrasound image, the operator presses the sound-velocity switching button of the input device 3, similarly to the first embodiment.

Accordingly, the processing by the transmission-reception control unit 151, the image-creation control unit 152, and the display control unit 153 is again started. However, according to the second embodiment, the sound-velocity switching regulation unit 151a regulates switching of the set sound velocity after regulating so as to include the optimal sound velocities determined by the optimal sound-velocity determining unit 154 in the switching route.

For example, as shown in FIG. 9, similarly to the first embodiment, assuming that the set sound velocity at the present moment is "1540 m/sec", and a variable range of the set sound velocity is "from 1400 m/sec to 1600 m/sec"; when the sound-velocity switching button is pressed, the sound-velocity switching regulation unit 151a regulates switching of the set sound velocity based on that time-intervals of switching the sound velocity are regular, and value-intervals of switching the sound velocity value are constant (interval 20 m/sec in the figure).

In other words, as shown in FIG. 9, the sound-velocity switching regulation unit 151a regulates the switching of the set sound velocity in the switching zone through a switching route that: the set sound velocity is increased by the interval 20 m/sec from "'1540 m/sec" to "1600 m/sec" at regular time-intervals; the set sound velocity is decreased by the interval 20 m/sec from "1600 m/sec" to "1400 m/sec" at regular time-intervals; and furthermore, the set sound velocity is switched by the interval 20 m/sec from "1400 m/sec" to "1425 m/sec" that is the optimal sound velocity at regular time-intervals.

The operator then refers to ultrasound images sequentially displayed on the monitor 2 during the switching zone, and visually determines the set sound velocity of an ultrasound image of which the lateral resolution of a portion to be focused becomes optimal. The operator then sets a set sound velocity (1480 m/sec) that is visually determined as optimal, manually with the keyboard of the input device 3, for example, as shown in FIG. 9.

When the set sound velocity is received from the operator via the input device 3, the image-creation control unit 152 sets a reception delay time calculated by the reception delay-time setting unit 151b by using the received set sound velocity, into the transmitting-receiving unit 11. Accordingly, the signal processing unit 12 and the image creating unit 13 create ultrasound images using the reception delay time corresponding to the set sound velocity that is determined as optimal by the operator, and the created ultrasound images are displayed on the monitor 2 by the control by the display control unit 153.

Although the embodiment is explained above in a case where the optimal sound velocity determined by the optimal sound-velocity determining unit 154 is positioned at the end of the switching route, the embodiment is not limited to this, and can be in a case where as long as the optimal sound velocity determined by the optimal sound-velocity determining unit 154 is included, it can be positioned at the beginning or in a middle of the switching route.

Moreover, the embodiment is explained above in a case where the switching route is regulated so as to include an average calculated from all of the sound velocities each of which the optimal sound-velocity determining unit 154 determines as the optimal sound velocity in each small area, the embodiment is not limited to this. For example, the embodiment can be in a case where the switching route is regulated so as to include all of the sound velocities each of which the optimal sound-velocity determining unit 154 determines as the optimal sound velocity in each small area. Alternatively, the embodiment can be in a case where the switching route is regulated so as to include, for example, "n" average values that sound velocities determined by the optimal sound-velocity determining unit 154 as optimal sound velocities in respective small areas are averaged with respect to "n" areas divided along the ultrasound-beam transmission direction, respectively.

Processing by the ultrasound diagnosis apparatus according to the second embodiment is explained below with reference to FIGS. 10A and 10B. FIGS. 10A and 10B are flowcharts for explaining ultrasound-image display processing by switching of set sound velocity of the ultrasound diagnosis apparatus according to the second embodiment.

As shown in FIGS. 10A and 10B, according to the ultrasound diagnosis apparatus of the second embodiment, after the ultrasound probe 1 transmits an ultrasound beam and an imaging target portion of the subject P becomes ready to be scanned, and then when the optimization button of the input device 3 is pressed by the operator (Yes at Step S301); a plurality of ultrasound images corresponding to respective reception delay times calculated from respective set sound velocities is created by the control by the transmission-reception control unit 151 and the image-creation control unit 152.

The optimal sound-velocity determining unit 154 then calculates a contrast value between the created ultrasound images, thereby determining an optimal sound velocity (Step S302).

After that, when the sound-velocity switching button of the input device 3 is pressed by the operator (Yes at Step S303); by the control by the image-creation control unit 152, the image creating unit 13 creates an ultrasound image using a reception delay time calculated from the initial set sound velocity (S0) that is the set sound velocity at the present moment (Step S304).

The monitor 2 then displays the ultrasound image created at Step S304, by the control by the display control unit 153 (Step S305).

Subsequently, if a value-interval of switching the sound velocity value is the "interval 20 m/sec", the sound-velocity switching regulation unit 151a calculates the set sound velocity "S" to be set next at "S=S0+20" (Step S306); and determines whether the calculated "S" is a larger value than "Smax" that is the maximum value in the variable zone (Step S307).

If the calculated "S" is equal to or smaller than "Smax" that is the maximum value in the variable zone (No at Step S307); by the control by the image-creation control unit 152, the image creating unit 13 creates an ultrasound image by using a reception delay time calculated from the set sound velocity (S) (Step S308).

The monitor 2 then displays the ultrasound image created at Step S308, by the control by the display control unit 153 (Step S309).

After that, the sound-velocity switching regulation unit 151a renews the set sound velocity (S) to be set next to "S=S+20" (Step S310); returns to Step S307, and determines whether the renewed "S" is a larger value than "Smax".

By contrast, if "S" calculated at Step S306 or Step S310 is a larger value than "Smax" (Yes at Step S307); the sound-velocity switching regulation unit 151a renews the set sound velocity (S) to be set next to "S=S−20" (Step S311); and determines whether the renewed "S" is a smaller value than "Smin" that is the minimum value in the variable zone (Step S312).

If the calculated "S" is equal to or larger than "Smin" (No at Step S312); by the control by the image-creation control unit 152, the image creating unit 13 creates an ultrasound image by using a reception delay time calculated from the set sound velocity (S) (Step S313); and the monitor 2 displays the ultrasound image created at Step S313, by the control by the display control unit 153 (Step S314).

The sound-velocity switching regulation unit 151a then returns to Step S111 and renews the set sound velocity (S) to be set next to "S=S−20", and determines whether the renewed "S" is a smaller value than "Smin" that is the minimum value in the variable zone at Step S312.

By contrast, if "S" calculated at Step S311 is a smaller value than "Smin" (Yes at Step S312); the sound-velocity switching regulation unit 151a renews the set sound velocity (S) to be set next to "S=S+20" (Step S315); and determines whether the renewed "S" is a larger value than "S0" (Step S316).

If the renewed (S) is equal to or smaller than "S0" (No at Step S316); by the control by the image-creation control unit 152, the image creating unit 13 creates an ultrasound image by using a reception delay time calculated from the set sound velocity (S) (Step S317); and the monitor 2 displays the ultrasound image created at Step S317, by the control by the display control unit 153 (Step S318).

The sound-velocity switching regulation unit 151a then returns to Step S315, and renews the set sound velocity (S) to be set next to "S=S+0"; and determines whether the renewed (S) is a larger value than "S0" at Step S316.

By contrast, if the renewed (S) is a larger value than "S0" (Yes at Step S316); the sound-velocity switching regulation unit 151a renews the set sound velocity (S) to be set next to the optimal sound velocity determined by the optimal sound-velocity determining unit 154 at Step S302 (Step S319).

By the control by the image-creation control unit 152, the image creating unit 13 then creates an ultrasound image by using a reception delay time calculated from the set sound velocity (S=optimal sound velocity) (Step S320); the monitor 2 displays the ultrasound image created at Step S313, by the control by the display control unit 153 (Step S321); and then as the switching zone is counted as ended, the processing is terminated.

The reception delay-time setting processing by the ultrasound diagnosis apparatus according to the second embodiment is similarly to the reception delay-time setting processing by the ultrasound diagnosis apparatus according to the first embodiment explained above with reference to FIG. 5, except that when set sound velocity is not received from the operator, a reception delay time calculated from the optimal sound velocity determined by the optimal sound-velocity determining unit 154 is set in the transmitting-receiving unit 11, therefore explanation is omitted.

As described above, according to the second embodiment, ultrasound images including an ultrasound image using a reception delay time calculated from a sound velocity determined as an optimal sound velocity in a switching zone can be sequentially displayed, and the operator can confirm whether the lateral resolution of a portion to be focused on the ultrasound image of an optimal sound velocity is actually optimal.

The first and the second embodiments described above are explained in a case where ultrasound images sequentially created by the control by the transmission-reception control unit 151 and the image-creation control unit 152 are sequentially displayed in real time on the monitor 2 by the control by the display control unit 153. A third embodiment is explained below in a case where ultrasound images sequentially created by the control by the transmission-reception control unit 151 and the image-creation control unit 152 are once stored in the image memory 14, and then displayed on the monitor 2 anew by the control by the display control unit 153, with reference to a flowchart shown in FIG. 11. FIG. 11 is a flowchart for explaining reception delay-time setting processing of an ultrasound diagnosis apparatus according to the third embodiment.

The ultrasound diagnosis apparatus according to the third embodiment can be in a case where the ultrasound diagnosis apparatus executes the ultrasound-image display processing by switching set sound velocity (see FIGS. 4 and 5), similarly to the ultrasound diagnosis apparatus according to the first and the second embodiment; or in a case where only processing other than the ultrasound-image display processing in FIGS. 4 and 5 is performed. In either of the cases, the image memory 14 stores a plurality of ultrasound images sequentially created via switching routes.

Precisely, as shown in FIG. 11, in the ultrasound diagnosis apparatus according to the third embodiment, when a request for image display is received from the operator via the input device 3 (Yes at Step S401); the monitor 2 displays ultrasound images sequentially read from the image memory 14, in cine display, by the control by the display control unit 153 (Step S402).

The image-creation control unit 152 then determines whether ultrasound image is selected as the freeze button of the input device 3 is pressed by the operator who refers to ultrasound images displayed in cine display on the monitor 2 (Step S403).

If ultrasound image is not selected (No at Step S403); the display control unit 153 controls display such that the cine display is continued on the monitor 2 (Step S404); and the image-creation control unit 152 continues determination processing at Step S403.

By contrast, if an ultrasound image is selected (Yes at Step S403); the image-creation control unit 152 controls the reception delay-time setting unit 151b, thereby transmitting to the transmitting-receiving unit 11 a reception delay time that is used when the selected ultrasound image is created (Step S405); and the processing is terminated. After that, by the control by the image-creation control unit 152, the image creating unit 13 creates an ultrasound image using the reception delay time corresponding to the set sound velocity determined as optimal by the operator.

The request for image display described above can be input by pressing the freeze button, and selection of an ultrasound image can be carried out by releasing the freeze button.

As described above, according to the third embodiment, ultrasound images created in a switching zone can be repeatedly displayed anew, accordingly, the lateral resolution of a portion focused on an ultrasound image can be surely optimized.

Figure 12A:
FIGS. 12A and 12B are schematic diagrams for explaining a modification of the embodiments.
Figure 12B:
Figure 14A:
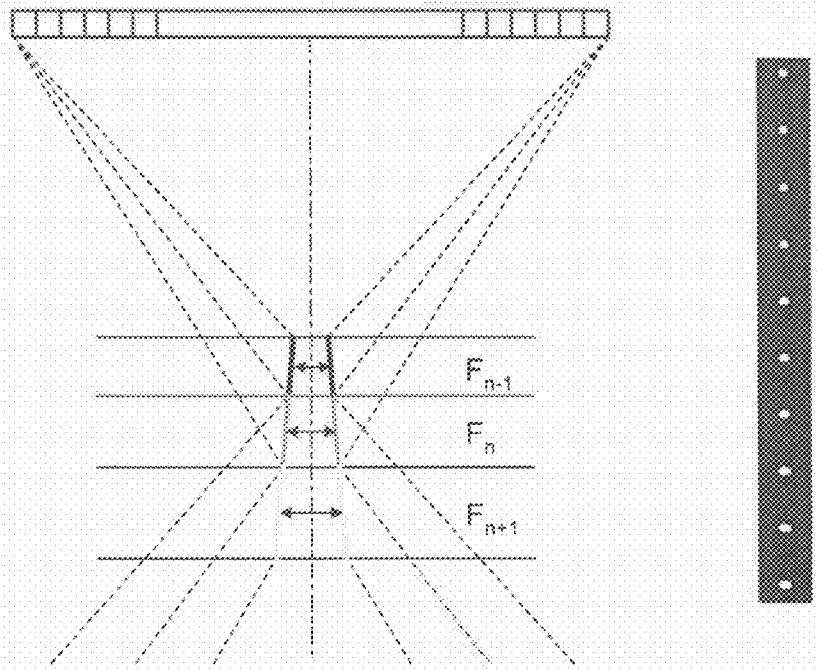
FIGS. 14A and 14B are schematic diagrams for explaining decrease in lateral resolution caused by a difference between a set sound velocity and a living-body sound velocity.
Figure 14B:
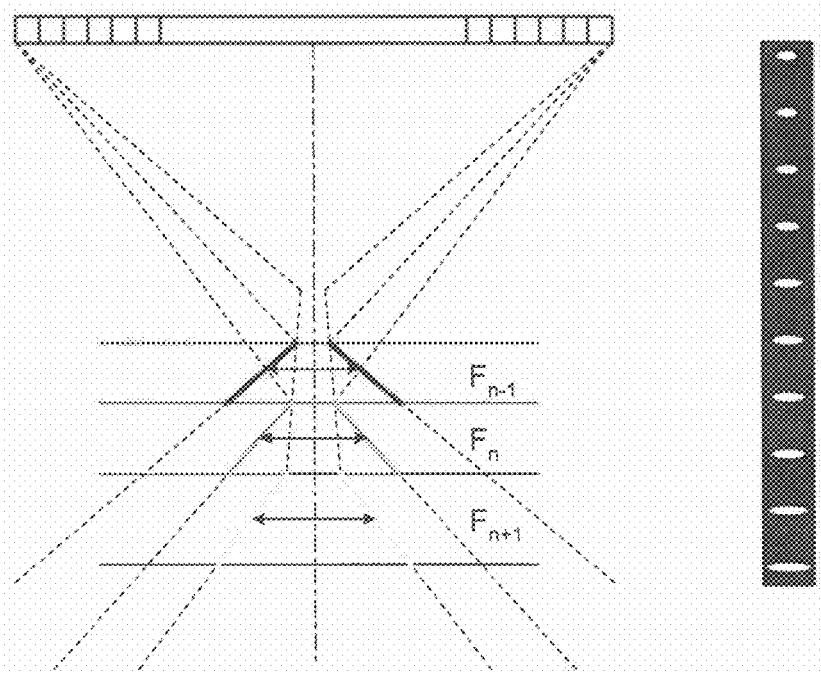

Each of the settings of a value-interval of switching the sound velocity value and a time-interval of switching the sound velocity explained in the first to the third embodiments described above can be arbitrarily changed by the operator. This is explained below with reference to FIGS. 12A and 12B. FIGS. 12A and 12B are schematic diagrams for explaining a modification of the embodiments.

For example, as shown in FIG. 12A, by turning a knob for adjusting sound velocity change included in the input device 3, the operator can change an initial setting of "interval 20 m/sec" with which the sound velocity value is switched to "1540, 1560, 1580, . . . ", to "interval 10 m/sec" with which the sound velocity value is to be switched to "1540, 1550, 1560, . . . ". Accordingly, the operator can searches for a sound velocity with which the lateral resolution becomes optimal, more finely.

Moreover, by turning a knob for adjusting time change included in the input device 3, the operator can change an initial setting of switching of the sound velocity value (1540, 1560, 1580, . . . ) to be performed every two frames, to that to be performed every four frames. Accordingly, the operator can refer to an ultrasound image per set sound velocity for a longer time, thereby being able to find a sound velocity with which the lateral resolution becomes optimal, more surely. The change of settings explained above with reference to FIGS. 12A and 12B is executed by, for example, control processing by the image-creation control unit 152.

Moreover, the setting of a switching route explained in the first to the third embodiment described above can be arbitrarily changed by an operator. For example, an operator can arbitrarily change the setting of a switching route such that after the sound velocity value is decreased from the set sound velocity set at the present moment toward the minimum value in a variable range, the sound velocity value is increased toward the maximum value in the variable range, and then the sound velocity value is decreased from the maximum value to the set sound velocity set at the present.

While certain embodiments have been described, these embodiments have been presented by way of example only, and are not intended to limit the scope of the inventions. Indeed, the novel apparatuses and methods described herein may be embodied in a variety of other forms; furthermore, various omissions, substitutions and changes in the form of the apparatuses and methods described herein may be made without departing from the spirit of the inventions. The accompanying claims and their equivalents are intended to cover such forms or modifications as would fall within the scope and spirit of the inventions.

What is claimed is:

1. A ultrasound diagnosis apparatus, comprising:
    an image creating unit configured to create an ultrasound image from data created by adding a reflected wave signal of an ultrasound wave transmitted to an imaging target portion of a subject by using a reception delay time calculated from a predetermined sound velocity being set as a sound velocity in the imaging target portion, wherein the predetermined sound velocity is in a variable range in which the ultrasound diagnosis apparatus can variably set sound velocities;
    an image-creation controller configured to sequentially switch the predetermined sound velocity being set at a present moment to one of a plurality of predetermined sound velocities in the variable range in which the ultrasound diagnosis apparatus can variably set sound velocities, based on an instruction from an operator received via an input unit, and to control the image creating unit so as to create a corresponding plurality of ultrasound images each using a reception delay time corresponding to each of the predetermined sound velocities to be switched; and
    a display controller configured to control a display to display the ultrasound images created by the image-creation controller on the display,
    wherein the input unit is configured to receive information from the operator who refers to the plurality of ultrasound images displayed on the display, the information indicating a preferred predetermined sound velocity among the predetermined sound velocities that the operator desires to set as the sound velocity in the imaging target portion.

2. The ultrasound diagnosis apparatus according to claim 1, further comprising:
    a sound-velocity determining unit configured to calculate a contrast value between each of the plurality of ultrasound images of the imaging target portion that is preliminarily created by the image creating unit by using a plurality of reception delay times calculated from the plurality of different predetermined sound velocities, and to determine the predetermined sound velocity corresponding to an ultrasound image of which the calculated contrast value is a maximum that, as an optimal sound velocity, is a set sound velocity corresponding to an ultrasound image of which the calculated contrast value becomes optimal,
    wherein the image-creation controller is configured to perform control such that the sound velocity determined as the optimal sound velocity by the sound-velocity determining unit is to be included in the set predetermined sound velocities to be switched, and to control the image creating unit so as to create the plurality of ultrasound images using respective reception delay times corresponding to the predetermined sound velocities to be switched.

3. The ultrasound diagnosis apparatus according to claim 2, further comprising a memory configured to store the ultrasound images created by control by the image-creation controller, wherein the display controller is configured to control the display such that the ultrasound images stored by the memory are displayed on the display, based on a display request from the operator received via the input unit.

4. The ultrasound diagnosis apparatus according to claim 2, wherein when any one of the ultrasound images is specified via the input unit by the operator who refers to the ultrasound images displayed on the display by the display controller, the image-creation controller is configured to perform control such that the reception delay time for creating the ultrasound image of the imaging target portion is set to the reception delay time that is used when creating the specified ultrasound image.

5. The ultrasound diagnosis apparatus according to claim 1, further comprising:
    a memory configured to store the ultrasound images created by control by the image-creation controller, wherein the display controller is configured to control the display such that the ultrasound images stored by the memory are displayed on the display, based on a display request from the operator received via the input unit.

6. The ultrasound diagnosis apparatus according to claim 5, wherein when any one of the ultrasound images is specified via the input unit by the operator who refers to the ultrasound images displayed on the display by the display controller, the image-creation controller is configured to perform control such that the reception delay time for creating the ultrasound image of the imaging target portion is set to the reception delay time that is used when creating the specified ultrasound image.

7. The ultrasound diagnosis apparatus according to claim 1, wherein when displaying the ultrasound images created by the image-creation controller on the display, the display controller is configured to control the display such that one of the sound velocity used for creation of each of the ultrasound images and an index value indicating the sound velocity used for creation of each of the ultrasound images is displayed together with each ultrasound image.

8. The ultrasound diagnosis apparatus according to claim 1, wherein when any one of the ultrasound images is specified via the input unit by the operator who refers to the ultrasound images displayed on the display by the display controller, the image-creation controller is configured to control such that the reception delay time for creating the ultrasound image of the imaging target portion is set to the reception delay time used when creating the specified ultrasound image.

9. The ultrasound diagnosis apparatus according to claim 1, wherein the image-creation controller is configured to perform control so as to regulate at least one of time-intervals of switching the set predetermined sound velocities to be switched and intervals of switching sound velocity values of the predetermined sound velocities to be switched, based on the instruction from the operator received via the input unit.

10. A method of setting sound-velocity, comprising:
    controlling, by an image-creation controller of an ultrasound diagnostic apparatus, an image creating unit configured to create an ultrasound image from data created by adding a reflected wave of an ultrasound wave transmitted to an imaging target portion of a subject by using a reception delay time calculated from a predetermined sound velocity being set as a sound velocity in the imaging target portion, wherein the predetermined sound velocity is in a variable range in which the ultrasound diagnosis apparatus can variably set sound velocities, so as to switch the predetermined sound velocity being set at a present moment to one of a plurality of predetermined sound velocities in the variable range in which a set sound velocity can be variably set, based on an instruction from an operator received via an input unit, and to create a corresponding plurality of ultrasound images using respective reception delay times corresponding to the plurality of predetermined sound velocities to be switched; and controlling, by a display controller, a display to display the ultrasound images created by the image-creation controller on the display, wherein the input unit is configured to receive information from the operator who refers to the plurality of ultrasound images displayed on the display, the information indicating a preferred predetermined sound velocity among the predetermined sound velocities that the operator desires to set as the sound velocity in the imaging target portion.

11. The method of setting sound-velocity according to claim 10, further comprising:

calculating, by a sound-velocity determining unit, a contrast value between each of the plurality of ultrasound images of the imaging target portion that is preliminarily created by the image creating unit by using a plurality of reception delay times calculated from the plurality of different predetermined sound velocities, and determining, by the sound-velocity determining unit, the predetermined sound velocity corresponding to an ultrasound image of which the calculated contrast value is a maximum that, as an optimal sound velocity, is a set sound velocity corresponding to an ultrasound image of which the calculated contrast value becomes optimal, wherein the image-creation controller is configured to perform control such that the sound velocity determined as the optimal sound velocity by the sound-velocity determining unit is to be included in the predetermined sound velocities to be switched, and to control the image creating unit so as to create the plurality of ultrasound images using respective reception delay times corresponding to the predetermined sound velocities to be switched.

12. The method of setting sound-velocity according to claim 11, further comprising storing, by a memory, the ultrasound images created by the image-creation controller, wherein the display controller is configured to control the display such that the ultrasound images stored by the memory are displayed on the display, based on a display request from the operator received via the input unit.

13. The method of setting sound-velocity according to claim 11, wherein when any one of the ultrasound images is specified via the input unit by the operator who refers to the ultrasound images displayed on the display by the display controller, the image-creation controller is configured to perform control such that the reception delay time for creating the ultrasound image of the imaging target portion is set to the reception delay time used when creating the specified ultrasound image.

14. The method of setting sound-velocity according to claim 10, further comprising:

storing, by a memory, the ultrasound images created by the image-creation controller, wherein the display controller is configured to control the display such that the ultrasound images stored by the memory are displayed on the display, based on a display request from the operator received via the input unit.

15. The method of setting sound-velocity according to claim 14, wherein when any one of the ultrasound images is specified via the input unit by the operator who refers to the ultrasound images displayed on the display by the display controller, the image-creation controller is configured to perform control such that the reception delay time for creating the ultrasound image of the imaging target portion is set to the reception delay time used when creating the specified ultrasound image.

16. The method of setting sound-velocity according to claim 10, wherein when displaying the ultrasound images created by control by the image-creation controller on the display, the display controller is configured to control the display such that one of the sound velocity used for creation of each of the ultrasound images and an index value indicating the sound velocity used for creation of each of the ultrasound images is displayed together with each ultrasound image.

17. The method of setting sound-velocity according to claim 10, wherein when any one of the ultrasound images is specified via the input unit by the operator who refers to the ultrasound images displayed on the display by the display controller, the image-creation controller is configured to perform control such that the reception delay time for creating the ultrasound image of the imaging target portion is set to the reception delay time used when creating the specified ultrasound image.

18. The method of setting sound-velocity according to claim 10, wherein the image-creation controller is configured to perform control so as to regulate at least one of time-intervals of switching the predetermined sound velocities to be switched and intervals of switching sound velocity values of the predetermined sound velocities to be switched, based on the instruction from the operator received via the input unit.

* * * * *

UNITED STATES PATENT AND TRADEMARK OFFICE
CERTIFICATE OF CORRECTION

PATENT NO. : 8,475,381 B2  
APPLICATION NO. : 12/824697  
DATED : July 2, 2013  
INVENTOR(S) : Akihiro Kakee et al.

It is certified that error appears in the above-identified patent and that said Letters Patent is hereby corrected as shown below:

On the title page, Item (73), the 2$^{nd}$ Assignee's Information is incorrect. Item (73) should read:

--(73) Kabushiki Kaisha Toshiba, Tokyo (JP);  
Toshiba Medical Systems Corporation, Otawara-shi (JP)--

Signed and Sealed this  
Third Day of September, 2013

Teresa Stanek Rea  
*Acting Director of the United States Patent and Trademark Office*